(12) United States Patent
Anastassov et al.

(10) Patent No.: US 11,890,361 B2
(45) Date of Patent: *Feb. 6, 2024

(54) ORAL CARE COMPOSITION COMPRISING CANNABINOIDS

(71) Applicant: APIRX Pharmaceutical USA, LLC, New York, NY (US)

(72) Inventors: George Anastassov, New York, NY (US); Lekhram Changoer, Ridderkerk (NL)

(73) Assignee: APIRx Pharmaceutical USA, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/920,065

(22) Filed: Jul. 2, 2020

(65) Prior Publication Data

US 2020/0330339 A1 Oct. 22, 2020

Related U.S. Application Data

(63) Continuation of application No. 16/184,747, filed on Nov. 8, 2018, now abandoned, which is a continuation of application No. 14/970,322, filed on Dec. 15, 2015, now Pat. No. 10,172,786.

(60) Provisional application No. 62/092,609, filed on Dec. 16, 2014.

(51) Int. Cl.
| | |
|---|---|
| *A61K 8/37* | (2006.01) |
| *A61K 8/92* | (2006.01) |
| *A61K 8/34* | (2006.01) |
| *A61K 8/49* | (2006.01) |
| *A61K 8/35* | (2006.01) |
| *A61Q 11/00* | (2006.01) |
| *A61K 8/19* | (2006.01) |
| *A61K 8/86* | (2006.01) |
| *A61K 8/25* | (2006.01) |
| *A61K 8/44* | (2006.01) |
| *A61K 8/46* | (2006.01) |
| *A61K 8/73* | (2006.01) |
| *A61K 31/352* | (2006.01) |
| *A61K 8/9717* | (2017.01) |
| *A61K 8/9789* | (2017.01) |

(52) U.S. Cl.
CPC .............. *A61K 8/19* (2013.01); *A61K 8/25* (2013.01); *A61K 8/345* (2013.01); *A61K 8/442* (2013.01); *A61K 8/463* (2013.01); *A61K 8/731* (2013.01); *A61K 8/86* (2013.01); *A61K 8/9717* (2017.08); *A61K 8/9789* (2017.08); *A61K 31/352* (2013.01); *A61Q 11/00* (2013.01); *A61K 2800/28* (2013.01)

(58) Field of Classification Search
CPC ....... A61Q 11/00; A61K 8/345; A61K 31/352
See application file for complete search history.

(56) References Cited

U.S. PATENT DOCUMENTS

| | | | | |
|---|---|---|---|---|
| 1,817,664 | A | * 8/1931 | Badanes | .......... A61K 8/19 424/49 |
| 4,547,362 | A | 10/1985 | Winston et al. | |
| 4,927,625 | A | * 5/1990 | Duckworth | .......... A61K 8/21 424/49 |
| 5,330,749 | A | 7/1994 | Giacin et al. | |
| 5,898,037 | A | * 4/1999 | Marx | .......... A61K 33/06 424/49 |
| 6,410,588 | B1 | 6/2002 | Feldmann et al. | |
| 6,491,899 | B1 | 12/2002 | Leinen et al. | |
| 10,172,786 | B2 | 1/2019 | Anastassov et al. | |
| 2005/0277694 | A1 | 12/2005 | Stock et al. | |
| 2006/0135599 | A1 | * 6/2006 | Symonds | .......... A61P 25/20 514/454 |
| 2008/0112901 | A1 | 5/2008 | MacDonald et al. | |
| 2009/0156484 | A1 | * 6/2009 | Valenti | .......... A61K 38/40 514/2.5 |
| 2009/0181080 | A1 | 7/2009 | Kottayil et al. | |
| 2011/0008094 | A1 | 1/2011 | Solan | |
| 2012/0021075 | A1 | 1/2012 | Umanskaya et al. | |
| 2012/0189561 | A1 | 7/2012 | Randive et al. | |
| 2012/0214766 | A1 | 8/2012 | Jones et al. | |
| 2013/0054044 | A1 | 2/2013 | Shaffer et al. | |
| 2013/0197710 | A1 | 8/2013 | Hansen | |
| 2013/0230469 | A1 | 9/2013 | Lewus et al. | |
| 2014/0094983 | A1 | 4/2014 | Dykeman et al. | |
| 2014/0166028 | A1 | 6/2014 | Fuisz et al. | |

(Continued)

FOREIGN PATENT DOCUMENTS

| | | |
|---|---|---|
| CN | 102895147 | 1/2013 |
| CN | 103784336 | 5/2014 |

(Continued)

OTHER PUBLICATIONS

Machine translation of KR 2012/0133135 A supplied by KIPO (Year: 2021).*
Google_scholar_search_Jul. 9, 2021_cannabidiol_mouth_rinse. (Year: 2021).*
International Search Report and Written Opinion in application No. PCT/EP2018/052555, dated Jan. 6, 2018.
Abir et al., "Antidepressant-like effect of Δ9-tetrahydrocannabinol and other cannabinoids isolated from *cannabis sativa*", L. Pharmacol. Biochem. Behav., vol. 95(4):434-442 (2010).
Eisohly et al., "Synthesis and antimicrobial activities of certain cannabichromene and cannabigerol related compounds", Journal of Pharmaceutical Sciences, vol. 71(12):1319-1323 (1982).

(Continued)

*Primary Examiner* — Michael P Cohen
(74) *Attorney, Agent, or Firm* — Knobbe Martens Olson & Bear LLP

(57) ABSTRACT

This application discloses oral care compositions comprising cannabinoids, preferably cannabidiol and/or cannabigerol. The oral care composition disclosed in this application may be a tooth paste, a tooth powder, or a mouthwash solution. The oral care composition may be used to treat oral infectious disease, including periimplantitis, periodontitis, oral mucositis, and dental pain.

21 Claims, No Drawings

(56) References Cited

U.S. PATENT DOCUMENTS

| | | |
|---|---|---|
| 2014/0172182 A1 | 6/2014 | Subbotin et al. |
| 2016/0043581 A1 | 2/2016 | Ito |
| 2016/0218511 A1 | 7/2016 | Li et al. |
| 2016/0334821 A1 | 11/2016 | Lee et al. |
| 2017/0063125 A1 | 3/2017 | Jezierski, Jr. |
| 2018/0060772 A1 | 3/2018 | Koch |
| 2019/0076349 A1 | 3/2019 | Anastassov et al. |

FOREIGN PATENT DOCUMENTS

| | | |
|---|---|---|
| KR | 20120133135 A * | 12/2012 |
| WO | WO 2005/079582 | 9/2005 |
| WO | WO 2016/150815 | 9/2016 |
| WO | WO 2018/145998 | 8/2018 |

OTHER PUBLICATIONS

International Search Report and Written Opinion in application No. PCT/US2015/066099, dated Apr. 11, 2016.
International Preliminary Report on Patentability for application No. PCT/US2015/066099, dated Mar. 7, 2016, in 6 pages.
Partial European Search Report for application No. EP 21165551.9, dated Jul. 14, 2021, in 5 pages.
Khan et al., "Antibacterial properties of hemp and other natural fibre plants: A review", BioResources, vol. 9(2):3642-3659 (2014).
Nadulski et al., "Simultaneous and sensitive analysis of THC, 11-OH-THC, THC-COOH, CBD, and CBN by GC-MS in plasma after oral application of small doses of THC and cannabis extract", Journal of Analytical Toxicology, vol. 29:782-789 (2005).
Nagarkatti et al., "Cannabinolds as novel anti-inflammatory drugs", Future Med. Chem. vol. 1(7): 1333-1349 (2009).

\* cited by examiner

ORAL CARE COMPOSITION COMPRISING CANNABINOIDS

CROSS-REFERENCE TO RELATED APPLICATIONS

This application is a continuation of U.S. application Ser. No. 16/184,747, filed on Nov. 8, 2018, which is a continuation of U.S. application Ser. No. 14/970,322, filed on Dec. 15, 2015, now U.S. Pat. No. 10,712,786, which claims the benefit of U.S. Provisional Application No. 62/092,609, filed Dec. 16, 2014. Each of the above-referenced patent applications is incorporated by reference in its entirety.

BACKGROUND OF THE INVENTION

Field of the Invention

The present invention relates to cannabinoid oral care compositions, specifically dentifrice in paste and powder form and mouthwash, methods to prepare the dentifrice and mouthwash, and methods to administer the dentifrice or mouthwash to a human subject. The present invention also relates to methods to treat oral infectious conditions using these oral care compositions.

Description of the Related Technology

Dentifrices are used with toothbrushes to clean and polish teeth. They come in powder, paste, liquid, or gel form, the most popular of which are known as toothpaste and tooth powder, both discussed below. People mainly use dentifrices to prevent dental plaque and remove food debris after eating.

Toothpastes are made up of abrasives, binders, surfactants, and humectants; dentists normally recommend toothpaste that also contains fluoride. While the main purpose of toothpaste is to maintain oral hygiene by cleaning teeth and removing food particles, toothpastes can also be manufactured to help freshen breath and whiten teeth. Early toothpaste began with the Greeks followed by the Romans, which was then imported into 9th Century Persia. Modern toothpaste began to appear in the late 19th Century, and fluoride was first added into toothpaste in the 1890's.

Toothpaste is manufactured typically by first preparing the liquid base, which is made up of water, sorbitol/glycerin, and other liquid ingredients. Rheology modifiers may be premixed with a non-aqueous liquid ingredient such as glycerin or flavoring oil, or dry blended with other powder ingredients to aid dispersion. The active ingredients, sweeteners, and preservatives are added and dispersed. The abrasive is then added, followed by flavoring and coloring agents. Finally, a foaming agent is added under slow speed agitation to avoid foaming.

Tooth powders are manufactured similarly to toothpastes, but without the liquid ingredients, giving only powder as the final product. Other ingredients such as flavoring oils can be added as preferred by the manufacturer.

Dental caries are common infectious diseases affecting billions of people in the world. Dental hygiene, including frequent teeth brushing and use of fluoride-containing dentifrice and/or mouthwash, improves dental health. Fluoride compounds are commonly added into dentifrices for anti-bacterial purposes. Fluoride compounds also act to reinforce the calcium structure of teeth, by inhibiting the initiation of dental caries. However, an excessive dosage of fluoride compounds can lead to white spots on teeth.

Bacteria present in the oral cavity are mostly *Streptococcus mutans*, *Escherichia coli*, and *Candida albicans*. *S. mutans* infects the throat, causing "strep throat," *E. coli* causes digestive tract infections, while *C. albicans* promotes dental caries. For these reasons, anti-bacterial toothpaste is manufactured. Common anti-bacterial toothpaste additives include triclosan and chlorhexidine. There have been some concerns that triclosan may cause hormone imbalance in animals. Most importantly, anti-bacterial additives are believed to cause anti-bacterial resistant bacteria to spread.

The cannabis plant has many naturally occurring substances that are of great interest in the fields of science and medicine. Isolated compounds from the cannabis plant include $\Delta^9$-tetrahydrocannabinol (THC), cannabidiol (CBD), cannabichromene (CBC), cannabigerol (CBG), cannabidivarin (CBDV), among other compounds. While THC has psychoactive effects, CBD, CBC, CBG, and CBDV do not. Isolated compounds from the cannabis plant are called cannabinoids. There are a total of eighty-five (85) cannabinoids that have been isolated from the cannabis plant. Many researchers have confirmed the medicinal value of cannabinoids. Cannabinoids have been investigated for possible treatment of seizures, nausea, vomiting, lack of appetite, pain, arthritis, inflammation, and other conditions.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1 S,6 S)-3-methyl-6-(prop-1-en-2-yl)cyclo-hex-2-enyl)-5-pentyl-benzene-1,3-diol). CBC has the IUPAC nomenclature of 2-methyl-2-(4-methylpent-3-enyl)-7pentyl-5-chromenol. These are among the most prominent compounds in the family of compounds extracted from the cannabis plant referred to as cannabinoids.

Cannabinoids may be isolated by extraction or cold pressing of cannabis plants. Plants in the cannabis genus include *Cannabis sativa*, *Cannabis ruderalis*, and *Cannabis indica*. These plants are the natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((−)-(6aR,10aR)-6,6,9-trimythel-3-pentyl-6a,7,8,10a-tetrahydro-6H-benzo[c]chromen-1-01)). These synthetic cannabinoids are investigated for medicinal purposes. The U.S. Food and Drug Administration approved nabilone for treatment of chemotherapy-induced nausea and vomiting. In the United States, nabilone is marketed under the name Cesamet®.

Cannabidiol from hemp is marketed in the United States. Various products containing cannabidiol have been marketed in recent years. Cannabidiol may be consumed by ingestion, by inhalation, or by transdermal delivery.

CBD, CBG, and THC have anti-bacterial properties, with fast acting mechanisms. These cannabinoids are anti-bacterial, with a minimum inhibitory concentration at between 0.5-2 µg/ml for various *Staphylococcus aureus* strains.

SUMMARY

The present invention is directed at an oral care composition, specifically a dentifrice and a mouthwash solution containing at least one cannabinoid having anti-bacterial properties. The at least one cannabinoid is present in an amount adequate to give anti-bacterial properties to the dentifrice; while at the same time is unlikely to cause an overdose of anti-bacterial compounds in dentifrice. The present invention also relates to methods to treat oral infectious diseases using the dentifrice and/or mouthwash solution comprising cannabinoids.

Abbreviations

CBC: Cannabichromene
CBDV: Cannabidivarin
CBD: Cannabidiol
CBG: Cannabigerol
IUPAC: International Union of Pure and Applied Chemistry
THC: Tetrahydrocannabinols
W/w: weight/weight

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol, (−)-(3 S,4S)-7-hydroxy-delta-6-tetrahydrocannabinol-1,1-dimethylheptyl, (+)-(3 S,4S)-7-hydroxy-$\Delta$-6-tetrahydrocannabinol, and $\Delta^8$-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl-2-cyclohexen-1-yl]-5-pentyl-1,3-benzendi-ol, and 4-(1,1-dimethylheptyl)-2,3'-dihydroxy-6'-$\alpha$-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with a trace amount of THC or from cannabis extract using high-CBD cannabis cultivars.

The word "cannabigerol" refers to cannabigerol and cannabigerol derivatives. As used in this application, cannabigerol is derived from industrial hemp extract with a trace amount of THC or from cannabis extract.

Toothpaste is manufactured by producing a prewetted binder with a humectant, and then dispersing the mixture into the liquid phase of the formulation. The entire mixture is mixed in a mixer to form a uniform paste. Alternatively, the binder is premixed with solid abrasives and then introduced into a mixing liquid phase of the formulation.

Cannabinoids used in this embodiment may be in liquid form, as a natural constituent of hemp oil or cannabis oil. Hemp oil or cannabis oil is harvested by cold pressing the seeds and the plants of the *Cannabis sativa* species. The resulting oil is extracted using $CO_2$ extraction or solvent extraction process, and may be further concentrated by distillation. Choice of cultivars may give different cannabinoid concentrations, but preferably, the targeted cannabinoids are cannabidiol (CBD) and cannabigerol (CBG). Other cannabinoids such as THC and cannabichromene (CBC) may also be present in hemp oil or cannabis oil. Further isolation of these cannabinoids may result in solid, purified cannabinoids.

In a preferred embodiment, toothpaste is manufactured with one or more cannabinoids incorporated for anti-bacterial effects. In this embodiment, the one or more cannabinoids are naturally derived or artificially derived.

When cannabinoids are provided as hemp oil or cannabis oil, the hemp oil or cannabis oil may contain up to 85% impurities, including fatty acids and other plant impurities. The extracted oil is then distilled to increase the cannabinoid concentration. Impurities in hemp oil and cannabis oil may be fatty acids such as linoleic acid and $\alpha$-linoleic acid, which are natural components of hemp oil or cannabis oil, $\beta$-caryophyllene, myrcene, and $\beta$-sitosterol.

In this embodiment, cannabinoids provided as hemp oil or cannabis oil may contain impurities in an amount of less than 85%, less than 80%, less than 75%, less than 70%, less than 65%, less than 55%, less than 50%, less than 45%, less than 40%, or less than 35% by weight.

While many cannabinoids may have anti-bacterial properties, including $\Delta^9$-tetrahydrocannabinols, non-psychoactive cannabinoids are preferred in this invention such that the embodiments may be used by all consumers. It is to be appreciated that psychoactive cannabinoids are included within the scope of the invention in certain embodiments, in cases where the psychoactive effect is unimportant.

When the oily form of cannabinoids is used, the viscosity of the oil is high, usually in a paste-like matrix. The cannabinoid-containing oil is combined with a binder and a humectant before introduction into the liquid phase. Alternatively, the cannabinoid oil is premixed with the binder and a solid abrasive before introduction into the liquid phase for mixing.

Hemp oil or cannabis oil with naturally occurring cannabinoids may have more than one cannabinoids. When hemp oil or cannabis oil is used to incorporate cannabinoid into toothpaste, the total cannabinoid content of the cannabis oil or hemp oil after addition into the toothpaste is at 0.1% to 0.5% by weight.

Solid and isolated cannabinoids may also be used. Solid cannabinoids may be combined with the binder and a humectant before introduction into the liquid phase. Solid cannabinoid(s) may also be mixed with the binder and a solid abrasive prior to introduction into the liquid phase. Solid cannabinoids are present in the toothpaste at 0.1% to 0.5% by weight.

Abrasive agents used in toothpaste manufacturing according to this embodiment may be hydrated alumina, silica, water-insoluble sodium metaphosphate, tricalcium phosphate, calcium phosphate dihydrate, anhydrous dicalcium phosphate, calcium pyrophosphate, calcium carbonate, sodium bicarbonate, or aluminum silicate. Commercially available abrasive agents such as Zeodent 113, Zeodent 115, or Zeodent 116 (silica abrasive agents) may be used. A combination of abrasive agents may also be used. Abrasive agents may be present in this embodiment at between 5% and 15% by weight.

A thickener, such as Zeodent 163, may be used together with other cleansing silica materials to thicken the toothpaste to a desirable viscosity. The thickener is present in the toothpaste at between 2% and 15% by weight.

Binders used in toothpaste manufacturing may be chosen from plant gum such as guar gum or xanthan gum, sodium alginate, karaya gum, bentonite, carrageenan, blanose cellulose gum, methylcellulose, and PEG-1500. The amount of binder present in this toothpaste may be at 0.2% to 2.5% by weight.

Humectants may retain water in the toothpaste matrix and keep toothpaste from drying out. Sorbitol, glycerin, and propylene glycol may be used as humectants. Glycerin and sorbitol may also give the sweet taste to the toothpaste as a whole.

Sorbitol may be present in this toothpaste at a 70% aqueous solution. In a toothpaste composition, sorbitol solution may be present at between 25% and 75% by weight of the toothpaste.

Where glycerin is used as a humectant, glycerin may be present at between 25% and 75% by weight of the toothpaste. Glycerin has a sweetness of about 60% that of table sugar and additional sweeteners may be added to improve the toothpaste's taste.

The toothpaste according to this embodiment may have one or more fluoride compounds to prevent dental caries. Suitable fluoride compounds may be sodium monofluorophosphate and sodium fluoride. The fluoride compound may be present in the toothpaste at 0.1% to 1% by weight.

In the toothpaste, the one or more cannabinoids may be present at 0.1% to 0.5% by weight, more specifically at 0.2% to 0.4% by weight. For naturally derived cannabinoids, wherein the hemp oil or cannabis oil has multiple cannabinoids, at least one cannabinoid may be present to comprise between 0.1% and 0.5% by weight of the toothpaste. For artificially derived cannabinoids, adding one isolated purified cannabinoid, preferably chosen from the group comprising of CBD, CBG, THC and CBC, is recommended. The amount of the artificial cannabinoid may be at 0.1% to 0.5% by weight of the toothpaste.

Lactoferrin may be added into the toothpaste in this embodiment at 0.1% to 0.5% by weight. Lactoferrin attacks biofilm bacteria and works as a wound dressing agent to speed up wound healing. In the oral cavity, biofilm bacteria are a major concern.

Anti-inflammation agents may be added into the toothpaste at 0.2% to 0.6% by weight. Magnesium sulfate has anti-inflammation properties as well as coagulant properties to stop bleeding, and may be added into the toothpaste according to this embodiment.

Foaming agents or surfactants may be added to toothpaste to create the foam appearance during brushing. Surfactants such as sodium lauryl sulfate, sodium lauryl sulfoacetate, dioctyl sodium sulfosuccinate, sulfolaurate, sodium lauryl sarcosinate, sodium stearyl fumarate, and sodium stearyl lactate may be added into the toothpaste. Commercially available foaming agents such as cocamidopropyl betaine (available as Tego Betain ZF, sold by Evonik Industries AG Personal Care) may also be used as surfactants.

Other components of the toothpaste may be used in sufficient amounts, including water, other preservatives, sweeteners, and flavoring oils.

Flavoring oils as used this embodiment may be wintergreen, peppermint, spearmint, cinnamon, orange, watermelon, citrus, peach, apricot, anise, vanilla, clove, green tea, caraway, eucalyptus, sage, thyme, bourbon, rye, or any suitable flavors. Multiple flavors may be added.

Coloring agents to give the toothpaste a desirable color may be added. Popular colors are white, blue, red, orange, and green. Coloring agents may be present in the toothpaste at 1% to 3% by weight.

Preservatives suitable for food products may be added into the toothpaste. Suitable preservatives include citric acid, trisodium citrate, alcohols, benzoates, and dichlorinated phenols. Citric acid and citrates are preferred preservatives. Preservatives may be present at 0.05% to 2% by weight.

Abrasive agents, humectants, binders, and cannabinoids may be combined and mixed in a container, forming the first phase. The liquid phase, or the second phase, including water, fluoride compounds, preservatives, coloring agents, sweeteners, and flavoring oils, may be combined and mixed. Then, the first phase may be mixed into the second phase and stirred well with a propeller. Temperature control to keep the mixture from drying out is desirable.

In another embodiment of this invention, tooth powder with cannabinoids added for anti-bacterial purposes is disclosed. Tooth powder may be used in the same manner as toothpaste. Tooth powder contains similar ingredients with toothpaste, but without water and binders.

In this embodiment, solid isolated cannabinoid(s) may be used in the manufacturing of dentifrices. Isolated cannabinoids may be in fine powder form and may be effective when combined into dentifrice powder. Grain size may be modified and adjusted to avoid sieving effects and separation of grains within the dentifrice powder.

In this embodiment, the tooth powder may contain one or more abrasive agents. The one or more abrasive agent may be chosen from a group comprising of baking soda, chalk, clay, activated carbon, or pumice powder.

One or more cannabinoids in powder form may be added into the tooth powder in this embodiment. One or more cannabinoids may be present in the tooth powder at 0.05% to 0.3% by weight.

Preferably, the cannabinoids added to tooth powder may be derived from natural sources. Hemp oil or cannabis oil with naturally occurring cannabinoids may be freeze dried, or granulated and purified, and the resulting powder, which is high in cannabinoids, may be added into tooth powder at 0.05% to 0.5% by weight.

Synthetic cannabinoids may also be added into tooth powder. Synthetic cannabinoids are typically in powder form and mix well into tooth powder. The proportion of synthetic cannabinoids added may be at 0.05% to 0.5% by weight.

The tooth powder may further comprise a sweetener for taste improvement purposes. Xylitol is the preferred sweetener as it is available in powder form and does not cause dental caries. Saccharin may also be used, but due to its strong sweet taste, the proportion added should be low. The proportion of the sweetener is according to taste, but preferably at 0.5% to 10% by weight of the tooth powder.

The tooth powder may further comprise other additives for flavor, such as sage, spearmint, peppermint essential oil, wintergreen essential oil, lemon oil, orange oil, anise oil, or cinnamon oil. Flavors are available in essential oil and may be combined into the tooth powder by mixing.

Components of the tooth powder according to this embodiment are mixed by a solid mixer for even distribution.

The toothpaste or tooth powder according to these embodiments is used by placing a sufficient quantity on a toothbrush. A human subject applies agitating force to his or her teeth using the toothbrush with the toothpaste or tooth powder. The human subject rinses his or her mouth with drinking water.

In another embodiment of this invention, a mouthwash solution comprising cannabinoids is provided. This cannabinoid mouthwash solution may have anti-bacterial properties and inhibits growth of harmful bacteria in the oral cavity.

In this embodiment, one or more cannabinoids may be added as isolated cannabinoids, either naturally or artificially derived. Isolated cannabinoids are in powder form and requires relatively smaller emulsifying capacity when mixed into a water/ethanol solution. Cannabinoids provided as hemp oil or cannabis oil may be incorporated, but preferably with higher emulsification load. The resulting mouthwash solution using hemp oil or cannabis oil may separate.

Cannabinoids as used in this embodiment are THC, CBD, and CBG, preferably CBD and CBG. A combination of different cannabinoids may be used in this embodiment. Cannabinoids are present in this embodiment at 0.5% to 4% by weight of the mouthwash solution.

If hemp oil or cannabis oil with high cannabinoid concentration is used, the total cannabinoid content added may be present at 0.5% to 4% by weight of the mouthwash. When hemp oil or cannabis oil is used, a combination of cannabinoids may be present.

The mouthwash solution may include surfactants. Suitable nonionic surfactants may be poly-ethoxylated sorbitol esters, polycondensates of ethylene oxide and propylene oxide, poly-ethoxylated hydrogenated castor oil (available as Eumulgin HRE40, sold by BASF). Suitable anionic surfactants are sodium dodecyl sulfate (sodium laurylsulfate), sodium laureth sulfate, sodium lauroyl sarcosinate, and potassium lauryl sulfate. Suitable amphoteric surfactants include, for example, long chain imidazoline and long chain alkyl betaines. Suitable cationic surfactants include D,L-2-pyrrolidone-5-carboxylic acid salt of ethyl-N-cocoyl-L-alginate and cocamidopropyl PG dimonium chloride phosphate. Surfactants may be present in this embodiment at 0.5% to 10% (w/w), more preferably at 0.5% to 5% (w/w).

The mouthwash solution may further include thickeners. Suitable thickeners may be methylcellulose, hydroxyalkylcellulose ethers, alkylcellulose ethers, hydroxypropyl methylcellulose, gum tragancanth, sodium carboxymethylcellulose, blanose cellulose gum (available as Blanose 7LF, sold by Ashland), polyvinyl pyrrolidone (available as Plasdone C-30, sold by Ashland), and carrageenan. Thickeners also act as emulsifiers to promote mixing in the suspension. The thickening agent may be present in the mouthwash solution at 0.5% to 5% (w/w).

The mouthwash solution preferably further comprises a humectant. Humectants retain water and prevent the solution from drying out. Suitable humectants may be chosen from a group comprising of glycerine, sorbitol, propylene glycol, and polyethylene glycol. A combination of more than one humectants may also be used. Humectants may be present in the mouthwash solution at 2% to 10% (w/w).

The mouthwash may further include cavity prevention and/or re-mineralization agents. Suitable cavity prevention or remineralization agents may be sodium monofluorophosphate and sodium fluoride. The cavity prevention agent may be present in the mouthwash solution at 0.01% to 0.5% (w/w).

The mouthwash according to this embodiment may further comprise an additional anti-bacterial agent such as lactoferrin. Lactoferrin attacks biofilm bacteria and acts as a wound-dressing agent to promote healing.

The mouthwash according to this embodiment may further comprise at least one flavor. Flavors as used this embodiment may be wintergreen, peppermint, spearmint, cinnamon, orange, watermelon, citrus, peach, apricot, anise, vanilla, clove, green tea, caraway, eucalyptus, sage thyme, bourbon, rye, or any suitable flavors. Multiple flavors may be added.

Coloring agents to give the mouthwash a desirable color may be added. Popular colors may be white, blue, orange, gold, and green. Coloring agents may be present in the mouthwash at 1% to 3% by weight.

Preservatives suitable for food products may be added into the mouthwash according to this embodiment. Suitable preservatives include citric acid, trisodium citrate, alcohols, sodium paraben, benzoates, and dichlorinated phenols. Preservatives may be present at 0.05% to 2% (w/w).

The mouthwash solution may have an aqueous base comprising water and ethanol. Ethanol increases solubility of powder cannabinoids. Ethanol may be present in this mouthwash at 5% to 20% (w/w).

The mouthwash solution may be used by a mammal, preferably a human being, by placing an appropriate amount of the mouthwash in the human subject's mouth, the human subject holds the mouthwash in the oral cavity for at least thirty (30) seconds, and the human subject spits the mouthwash out.

Various oral infectious diseases may be treated with cannabinoid oral care solutions due to their antibacterial, pain relieving, wound dressing, and anti-inflammation properties. Conditions treated by these cannabinoid oral care compositions may include periimplantitis, periodontitis, oral mucositis (especially oral mucositis caused by chemotherapy in cancer treatment), and dental pain.

Cannabinoid dentifrice, including cannabinoid toothpaste and cannabinoid tooth powder, may be used in teeth brushing at a therapeutically effective amount to treat periimplantitis, periodontitis, oral mucositis, and dental pain.

Cannabinoid mouthwash may be used in conjunction with, or separately from, cannabinoid dentifrice. A therapeutically effective amount of cannabinoid mouthwash may be held in the oral cavity of a human subject for at least thirty seconds before spitting out for treatment of periimplantitis, periodontitis, oral mucositis, and dental pain.

EXAMPLES

Example 1

This formulation makes 3000 grams of toothpaste. All ingredients are obtained and weighed according to Table 1.

The following ingredients are obtained: Glycerin 99% Ph Eur by Sigma-Aldrich, trisodium citrate.2 aq Ph Eur by Sigma-Aldrich, PEG-1500 by Sigma-Aldrich, Zeodent 113 (abrasive agent) and Zeodent 163 (thickener) by Huber Engineered Materials, Tego Betain ZF (foaming agent) by Prospector, Blanose CMC 12M31XP (binder) by Ashland.

Other ingredients are purified water, FD&C Blue No. 1 (0.2% solution) for coloring, methyl salicilate (wintergreen flavor), Flavor RV35640 (peppermint flavor), sodium methylparaben (preservative), citric acid (preservative), saccharine (flavor), xylitol (cavity prevention), magnesium sulfate 7.aq (anti-inflammation agent), sodium fluoride (remineralized agent), hemp oil with 3% w/w CBD and 17% w/w CBG (anti-bacterial agent, wound dressing agent), lactoferrin (anti-bacterial agent, wound dressing agent).

TABLE 1

Ingredients for cannabinoid toothpaste

| Raw Material | % (w/w) | Weight (g) |
| --- | --- | --- |
| Glycerine 99% Ph Eur | 56.0800 | 1682.4000 |
| Water | 15.0000 | 450.0000 |
| FD&C Blue No. 1 (0.2%-solution) | 2.0000 | 60.0000 |
| Methyl salicilate | 0.2000 | 6.0000 |
| Sodium methylparaben | 0.1500 | 4.5000 |
| Citric acid | 0.0800 | 2.4000 |
| Saccharine | 0.2500 | 7.5000 |
| Xylitol | 0.2500 | 7.5000 |
| Tri-Sodium Citrate.2aq Ph Eur | 0.3400 | 10.2000 |
| Magnesium Sulfate.7aq | 0.4300 | 12.9000 |
| Sodium fluoride | 0.2200 | 6.6000 |
| Hemp oil CBD/CBG (3%/17%) | 2.0000 | 60.0000 |
| Zeodent 113 | 8.0000 | 240.0000 |
| Zeodent 163 | 8.0000 | 240.0000 |
| Flavor RV35640 Peppermint | 1.5000 | 45.0000 |
| Tego Betain ZF | 3.0000 | 90.0000 |
| Blanose CMC12M31XP | 0.5000 | 15.0000 |
| PEG 1500 | 1.7500 | 52.5000 |
| Lactoferrin | 0.2500 | 7.5000 |
| Total | 100.0000 | 3000.0000 |

Stage 1: 450 grams of water are placed in the main mixer.

Stage 2: 15 grams of Blanose CMC 12M31XP, 240 grams of Zeodent 113 and Zeodent 163 each, and 60 grams of hemp oil (CBD/CBG 3%/17% w/w)) are dry mixed in a different vessel, then added into the main mixer. The main mixer mixes for 10 minutes and produces a cream-like paste.

Stage 3: In a different vessel, mix 1200 grams of the glycerin solution, saccharine, sodium fluoride, sodium methylparaben, xylitol, citric acid, trisodium citrate.2 aq Ph Eur, magnesium sulfate. 7 aq, PEG 1500, and lactoferrin. The vessel is heated to increase dissolution. This mixture is added into the main mixer and mixed for 15 minutes.

Stage 4: A mixture of Tego Betain ZF and the rest of the glycerin solution is added into the main mixer and mixed for 15 minutes.

Stage 5: Methyl salicilate and peppermint flavor are added into the main mixer and mixed for another 10 minutes. The toothpaste is then packed into tubes or pump containers.

Example 2

This formulation makes 100 grams of tooth powder.

TABLE 2

Ingredients for cannabinoid tooth powder

| Raw Material | % (w/w) | Weight (g) |
| --- | --- | --- |
| Baking soda | 39.7000 | 39.7000 |
| Clay | 30.0000 | 30.0000 |
| Cannabidiol (powder) | 0.1000 | 0.1000 |
| Cannabigerol (powder) | 0.2000 | 0.2000 |
| Xylitol | 20.0000 | 20.0000 |
| Peppermint oil | 10.0000 | 10.0000 |
| Total | 100.0000 | 100.0000 |

Weigh and combine baking soda, clay, cannabidiol, and xylitol according to the weight percentage given above. Mix well in a solid mixer; then add 10 grams of peppermint oil and mix for another 5 minutes. The resulting tooth powder is packaged into jars.

Example 3

This formulation makes 1000 g of mouthwash

TABLE 3

Ingredient for cannabinoid mouthwash

| Raw material | % (w/w) | Weight (g) |
| --- | --- | --- |
| Water | 81.010 | 810.100 |
| Ethanol | 10.000 | 100.000 |
| Glycerine 99% Ph Eur | 3.000 | 30.000 |
| Blanose 7LF | 0.300 | 3.000 |
| Tri-Sodium Citrate.2aq Ph Eur | 0.340 | 3.400 |
| Sodium methylparaben | 0.150 | 1.500 |
| Xylitol | 0.100 | 1.000 |
| Magnesium Sulfate.7aq | 0.050 | 0.500 |
| Plasdone C-30 | 1.000 | 10.000 |
| CBD/CBG (3%/17%) | 0.060 | 0.600 |
| CBG | 0.340 | 3.400 |
| Lactoferrine | 0.200 | 2.000 |
| Sodium laurylsulfate | 1.000 | 10.000 |
| Eumulgin HRE40 | 1.500 | 15.000 |
| Sodium fluoride | 0.050 | 0.500 |
| Methyl salicilate | 0.100 | 1.000 |
| Flavor RV35641 Peppermint | 0.300 | 3.000 |
| Citric acid | 0.500 | 5.000 |
| Total | 100.0000 | 1000.0000 |

All ingredients are obtained according to the list above. Mix all ingredients except for water and ethanol in a stainless steel container while mixing with a propeller. Add ethanol while continue to mix, then add water. The mixture is mixed for another 30 minutes. This formula makes 1000 g of mouthwash.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implements.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A cannabinoid toothpaste composition comprising:
   (a) at least one abrasive agent selected from the group consisting of abrasive silica, hydrated alumina, water-insoluble sodium metaphosphate, tricalcium phosphate, calcium phosphate dihydrate, anhydrous dicalcium phosphate, calcium pyrophosphate, calcium carbonate, sodium bicarbonate, and aluminum silicate;
   (b) at least one binder selected from the group consisting of guar gum, xanthan gum, sodium alginate, karaya gum, bentonite, carrageenan, blanose cellulose gum, and methylcellulose;
   (c) at least one humectant selected from the group consisting of sorbitol solution, glycerin solution, and propylene glycol;
   (d) at least one fluoridating agent selected from the group consisting of sodium fluoride, potassium fluoride, calcium fluoride, sodium fluorosilicate, acidulated phosphate fluoride, difluorosilane, sodium monofluorophosphate, ammonium fluorosilicate, and stannous fluoride;
   (e) at least one surfactant selected from the group consisting of sodium lauryl sulfate, sodium lauryl sulfoacetate, dioctyl sodium sulfosuccinate, sulfolaurate, sodium lauryl sarcosinate, sodium stearyl fumarate, and sodium stearyl lactate;
   (f) water;
   (g) a silicon dioxide-based thickener;
   (h) lactoferrin; and
   (i) one or more cannabinoids selected from the group consisting of $\Delta^9$-tetrahydrocannabinol, cannabidiol, and cannabigerol, wherein the one or more cannabinoids is present in an amount of 0.1 to 0.5 weight percent, and wherein lactoferrin is present in an amount of 0.1 to 0.5 weight percent.

2. The cannabinoid toothpaste of claim 1, further comprising one or more anti-inflammation agents.

3. The cannabinoid toothpaste of claim 2, wherein the anti-inflammation agent is magnesium sulfate.

4. The cannabinoid toothpaste of claim 2, further comprising one or more coloring agents.

5. The cannabinoid toothpaste of claim 2, wherein the one or more anti-inflammation agents is present in the composition in an amount of 0.2 to 0.6 weight percentage.

6. The cannabinoid toothpaste of claim 2, wherein the one or more anti-inflammation agents comprises magnesium sulfate.

7. The cannabinoid toothpaste of claim 1, further comprising a sweetener present in an amount of 0.5 to 10 weight percentage.

8. The cannabinoid toothpaste of claim 7, wherein the sweetener is xylitol.

9. The cannabinoid toothpaste of claim 1, further comprising one or more preservatives selected from the group consisting of citric acid, trisodium citrate, alcohols, benzoates, and dichlorinated phenols.

10. The cannabinoid toothpaste of claim 1, further comprising at least one flavor selected from the group consisting of spearmint, peppermint, wintergreen, cinnamon, orange, watermelon, citrus, peach, apricot, anise, vanilla, clove, green tea, caraway, eucalyptus, sage, thyme, bourbon, and rye.

11. The cannabinoid toothpaste of claim 1, wherein the one or more cannabinoids is cannabidiol.

12. The cannabinoid toothpaste of claim 1, wherein the one or more cannabinoids are present in the composition in an amount of 0.2 to 0.4 weight percentage.

13. The cannabinoid toothpaste of claim 1, wherein the abrasive agents are present in the composition in an amount of 5 to 15 weight percentage.

14. The cannabinoid toothpaste of claim 1, wherein the binder is present in the composition in an amount of 0.2 to 2.5 weight percentage.

15. The cannabinoid toothpaste of claim 1, wherein the thickener is present in the composition in an amount of 2 to 15 weight percentage.

16. The cannabinoid toothpaste of claim 1, wherein the sorbitol solution or glycerin solution is present in the composition in an amount of 25 to 75 weight percentage.

17. The cannabinoid toothpaste of claim 1, wherein the fluoridating agent is present in the composition in an amount of 0.1 to 1 weight percentage.

18. A cannabinoid toothpaste composition comprising:
   (a) at least one fluoridating agent selected from the group consisting of sodium fluoride, potassium fluoride, calcium fluoride, sodium fluorosilicate, acidulated phosphate fluoride, difluorosilane, sodium monofluorophosphate, ammonium fluorosilicate, and stannous fluoride;
   (b) a silicon dioxide-based thickener;
   (c) lactoferrin in an amount of 0.1 to 0.5 weight percent; and
   (d) one or more cannabinoids selected from the group consisting of $\Delta^9$-tetrahydrocannabinol, cannabidiol, and cannabigerol, wherein the one or more cannabinoids is present in an amount of 0.1 to 0.5 weight percent.

19. The cannabinoid toothpaste composition of claim 18, comprising cannabidiol and cannabigerol.

20. The cannabinoid toothpaste composition of claim 19, wherein the cannabidiol and cannabigerol is provided as a hemp oil comprising CBD/CBG at 3%/17% w/w.

21. The cannabinoid toothpaste composition of claim 19, further comprising $\Delta^9$-tetrahydrocannabinol.

* * * * *